United States Patent [19]

Sorkin

[11] Patent Number: 4,955,392

[45] Date of Patent: Sep. 11, 1990

[54] CONDOM OF THERMOPLASTIC ELASTOMER AND POLYOLEFIN FILM

[76] Inventor: Reuben Sorkin, 4721 University Dr., Coral Gables, Fla. 33146

[21] Appl. No.: 327,796

[22] Filed: Mar. 23, 1989

Related U.S. Application Data

[63] Continuation-in-part of Ser. No. 148,724, Jan. 25, 1988, Pat. No. 4,808,174, which is a continuation-in-part of Ser. No. 93,933, Sep. 8, 1987.

[51] Int. Cl.$^5$ .............................................. A61F 6/00
[52] U.S. Cl. ................................... 128/844; 128/918; 604/349
[58] Field of Search ............... 128/918, 844; 604/346, 604/347, 349–353; 428/35.5; 525/232, 240, 58

[56] References Cited

U.S. PATENT DOCUMENTS

| | | | |
|---|---|---|---|
| 3,677,225 | 7/1972 | Czirely | 604/352 |
| 4,517,970 | 5/1985 | Goepp et al. | 128/841 |
| 4,576,156 | 3/1986 | Dyck et al. | 128/844 |
| 4,642,267 | 2/1987 | Creasy et al. | 525/58 |
| 4,840,624 | 6/1989 | Lee | 604/349 |

*Primary Examiner*—Noah Kamen
*Attorney, Agent, or Firm*—Malloy & Malloy

[57] ABSTRACT

A condom of elastomeric film material composed of a vulcanized blend of thermoplastic elastomer with a low modulus polyolefin such as a low-density polyethylene wherein the condom includes a tubular length having a closed first end and an open second end and may also include an integral pubic shield about the open end with the tubular length being sized to receive the penis of a user and the pubic shield being adapted to overlay the pubic area of a user.

7 Claims, 2 Drawing Sheets

CONDOM OF THERMOPLASTIC ELASTOMER AND POLYOLEFIN FILM

This application is a continuation-in-part of earlier filed U.S. patent application Ser. No. 148,724, filed Jan. 25, 1988, now U.S. Pat. No. 4,808,174, which is a continuation-in-part of Ser. No. 07/093,933 filed Sept. 8, 1987, now abandoned.

FIELD OF THIS INVENTION

This invention relates to a condom of elastomeric film material which may include a pubic shield, the film material being a blend of vulcanized polyolefin thermoplastic elastomer or an olefinic blend of thermoplastic elastomer with a low modulus polyolefin such as ultra low-density polyethylen.

BACKGROUND OF THE INVENTION

There is a growing awareness of the seriousness of sexually transmitted diseases and the need for protection. Defects of latex condoms have become increasingly apparent. For example, it is estimated that about one-sixth of the users of latex condoms may nevertheless incur sexually transmitted diseases because of tears and improper use. This invention proposes a condom of elastomeric film as set forth more fully herein which reduces the risk of sexually transmitted disease and provides extra prevention. This is highly desirable especially in view of the seriousness of diseases such as AIDS, Herpes, Syphylis, Gonorrhea, Chalasmydia and other sexually transmitted diseases.

There are deficiencies in latex condoms in that the same may slip off the male organ after ejaculation because the penis becomes flaccid and shrinks to its normal size. When this happens, both partners are exposed to sexually transmitted diseases as well as pregnancy. Because the vagina provides an ideal growth culture media for all kinds of venereal disease, vaginal fluids should be avoided. The ordinary condom does not provide a water-tight seal at the base to protect the pubic area of a user from exposure of his body to sexually transmitted diseases. Also, because latex condoms may tear during coitus. Further, latex condoms should be stored under ideal conditions, for example, they cannot be exposed to extreme heat or cold. Hence, the condom of plastic material of the present invention provides an alternative to latex and is an improved product. The film material of the condom of the present invention is not adversely affected by products such as petroleum jelly which has a deliterious affect on latex condoms. Finally, latex and rubber condoms have a limited shelf life and, beyond this, become brittle and abrasive which is not typical of condoms of plastic material. This invention takes advantage of the favorable properties of plastics which are light in weight and very strong, have a good appearance and good feel. The product has favorable chemical resistance and generally good physical properties and is adaptable to mass production methods and is relatively inexpensive compared to latex.

OBJECT OF THE PRESENT INVENTION

It is, therefore, an object of this invention to provide an improved thin-walled condom of elastomeric film and comprises a tubular length having a closed first end and an open second end with the second end and tubular length being sized to jacket the penis of a user. Preferably, the condom also includes a pubic shield integral with it so that the pubic shield provides protection for an enlarged zone about the base of the penis and wherein an adhesive is preferably applied to the pubic shield for attachment of it to the body of a user during coitus.

It is a general object of this invention to provide an improved condom of the type described more fully hereinafter which is inexpensive to manufacture, well adapted for avoiding sexually transmitted diseases and which is highly desirable in the present environment characterized by sexually transmitted diseases and which is strong and durable and does not sacrifice sexual sensuality.

In accordance with these and other objects which will become apparent hereinafter, the instant invention will now be described with reference to the accompanying drawings in which:

DETAILED DESCRIPTION OF THE PREFERRED EMBODIMENT

Figure 1:
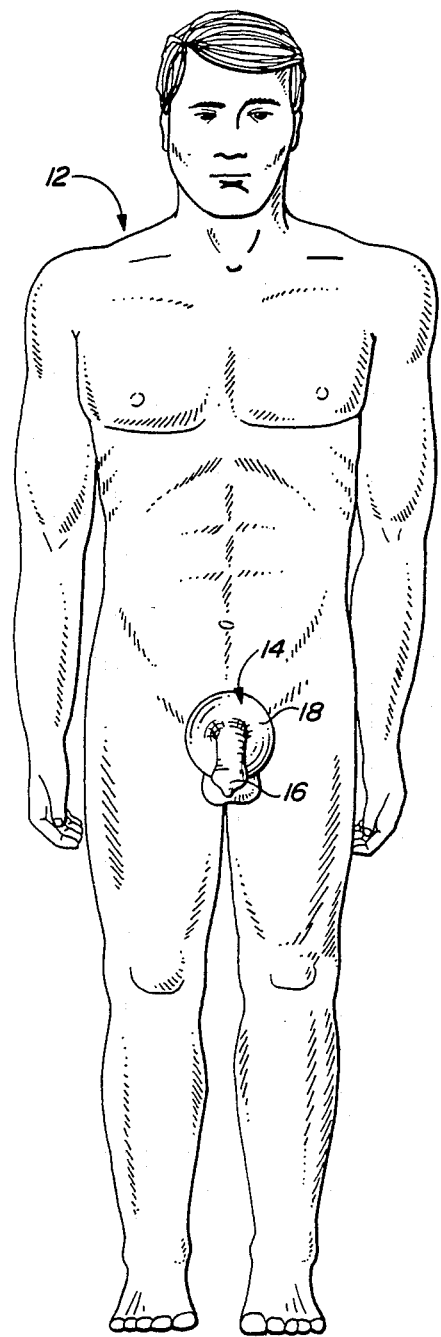
FIG. 1 illustrates an embodiment of the improved condom on the body of a wearer.
Figure 2:
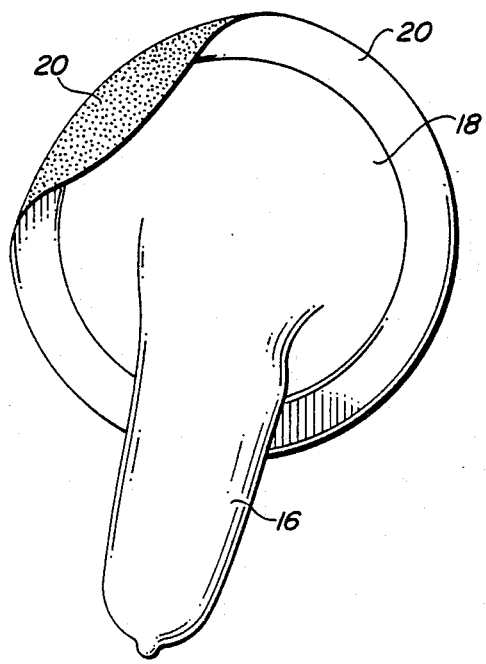
FIG. 2 illustrates the condom prior to use.
Figure 3:
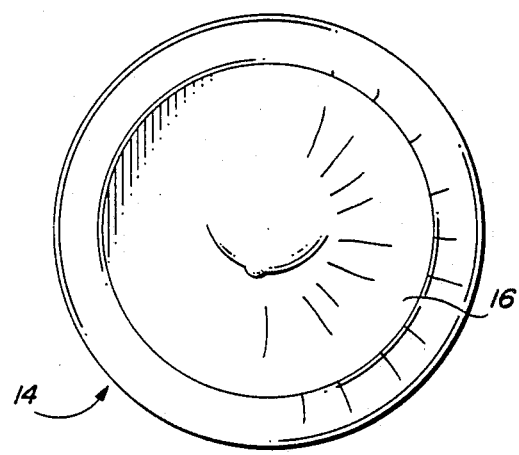
FIG. 3 illustrates the condom in a rolled condition.
Figure 4:
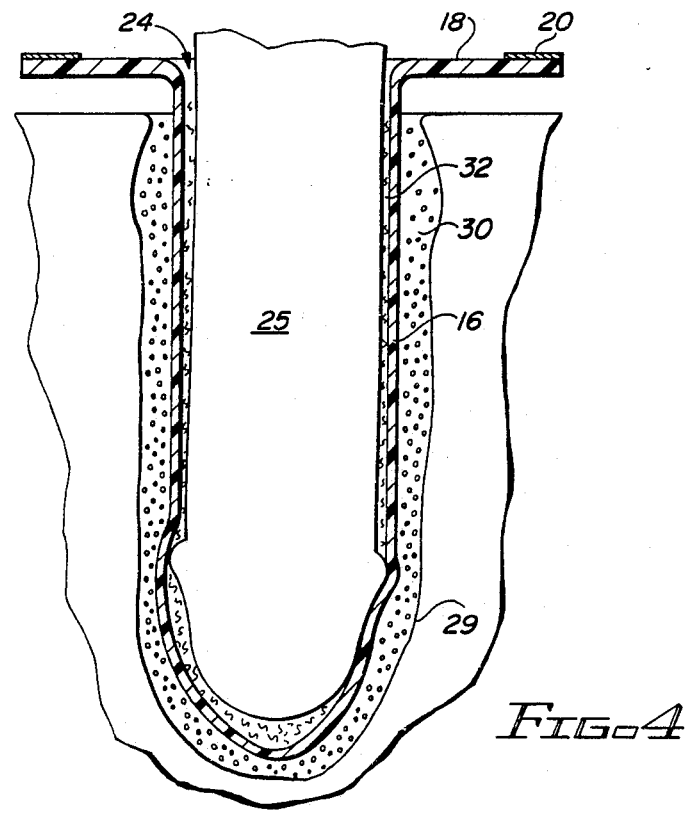
FIG. 4 illustrates the condom in use.

The present invention relates to an improved condom of elastomeric film material which includes an integral pubic shield. FIGS. 1 and 2 illustrate one embodiment of the invention. In FIG. 3, the condom is shown rolled upon itself. It may, however, be provided in packages in a collapsed attitude similar to the package used for surgical gloves for example. Preferably, the condom is provided in three sizes, small, medium, and large.

In the several views, the numerals designate similar parts in the several figures.

The film of the present invention includes a thermoplastic elastomer, an elastomer being generally a rubbery material which can be stretched substantially beyond its original length and, when relaxed, it will return to its original length. An important class of such elastomers are synthetic polymers including styrene-butadiene, polybutadiene, neoprene, butyl, polyisoprene, nitrile, and ethylene-propylene rubbers. The film of the present invention also includes a polyolefin, a term which includes polymers of ethylene, the alkyl derivatives of ethylene (the a-olefins), and the dienes. Preferably, the film includes polyethylene, which is a whitish, translucent polymer of moderate strength and high toughness. Commercially available forms range in crystallinity from 59–90%. The physical properties vary markedly with the degree of crystallinity and with the size and distribution of the crystalline regions. The densities of the products increase with increasing degrees of crystallinity and it is common to classify some of the commercial grades as low-density or ultra low-density types such as a density of 0.910–0.925 and 0.926–0.940. With increasing density, the products generally become stiffer and stronger with higher softening temperatures and higher resistance to penetration by liquids and gases while at the same time they lose some of their resistance to tear, impact and stress cracking. Ethylene is produced economically on a large scale by the cracking of aliphatic hydrocarbons found in petroleum. The monomer can be conveniently produced in smaller volumes by the catalytic dehydration of ethanol. One type of low-density polymer (low-density polyethylene) is formed by the polymerization of highly purified ethylene at about 150°-250° C. and at a high pressure of 20,000–35,000 p.s.i. in the presence of a very small amount of oxygen or organic peroxide. At the higher temperatures, the lowest-density polymer is formed and at the lower reaction temperatures, a more dense product is produced. A second type of low-density polymer (linear low-density polyethylene) is formed by the polymerization of ethylene and a-olefins. For the low-density material, the softening temperatures and the maximum temperature for continuous use are about 105°-115° C. and 75° C. Various types of polyethylene can be fabricated by many standard methods, for example, extrusion, blow molding (for film), and rotational and injection molding. For extrusion of film and blow molding, a high molecular weight is preferred, while a lower molecular weight is suitable for injection molding. It is known that at the same density and low-shear-stress viscosity in the melt, linear low-density polyethylene resins exhibit higher melting points, greater strengths, stiffness, elongations at break, and resistance to stress cracking than does low-density polyethylene.

The film utilized in the condom of the present invention preferably utilizes a linear low-density polyethylene material with a melt index of somewhere around 2, the melt index being a measure of molecular weight and also a measure of how much material flows through a spigot in ten minutes after being heated. This provides favorable tensile properties in relation to conventionally used latex material. In the preferred embodiment, the film is composed of a blend of vulcanized polyolefin thermoplastic elastomer or an olefinic blend of thermoplastic elastomer with a low modulus polypropylene, such as ultra low-density polyethylene. While the film exhibits similar texture and flexibility characteristic of latex rubber, it maintains an advantage in tensile properties. By blending a thermoplastic elastomer with the polyolefin, the impact and puncture resistance is enhanced substantially which is important in the condom application. It has also been found that the thermoplastic elastomer softens the polyolefin significantly allowing for a more comfortable product. Preferably, two congruent sheets are heat-sealed together. In summary, the film of the present invention utilizes a thermoplastic elastomeric blend to mimic the conventional latex condom properties. Preferably, the film of the present invention is of about 1 to 2 millimeters thick. The film for manufacturing the condoms is commercially available from the E. E. duPont de Nemours Company of Wilmington, Del. and also from the Exon Company of New Jersey.

In FIG. 1 a condom 14 of the type to be described is shown on a wearer 12. The condom 14 includes a tubular portion 16, see FIG. 2. It has a rounded, closed distal end that may include a smaller diameter reservoir portion at the terminal end zone. Also, the condom preferably includes a pubic shield 18 that is shown in a rolled stated in FIG. 3. In FIG. 3, the condom 14 is rolled onto itself and in FIG. 2 is shown in an unrolled attitude.

FIG. 1 shows the condom 14 disposed on the male user 12. In that figure, the pubic shield 18 is seen to protect the pubic area of the user. The tubular portion 16 has an open proximal end for inserting the penis 25 into a female opening 24. Preferably, a lubricant, such as the commercially available product, K.Y. jelly may be utilized on the exterior surface of the tubular portion 16 and, if desired, within the tubular portion. In a preferred embodiment, the condom is of two congruent sheets heat-sealed together and includes the shield for protecting the pubic area. The condom is made of the previously described blend of a vulcanized polyolefin thermoplastic elastomer or an olefinic blend of thermoplastic elastomer with a low modulus polyolefin such as ultra low-density polyethylene.

Preferably, the shield 18 extends radially outwardly from the tubular portion 16 at the proximal end at least a distance of one and one-half times the diameter of the opening at the proximal end. Preferably, the radial span of the shield is at least 2½ inches. A lubricant may be placed on the inside of the tubular portion 14 in order to assist the user in placing that portion onto his penis.

In addition to protecting the user from vaginal and other fluids 30 within the vagina 29 during intercourse, it is believed that after ejaculation and the collapse of the penis, the shield will better trap the ejaculated fluids and thereafter protect the other sexual partner from the male fluids 32.

Figure 5:
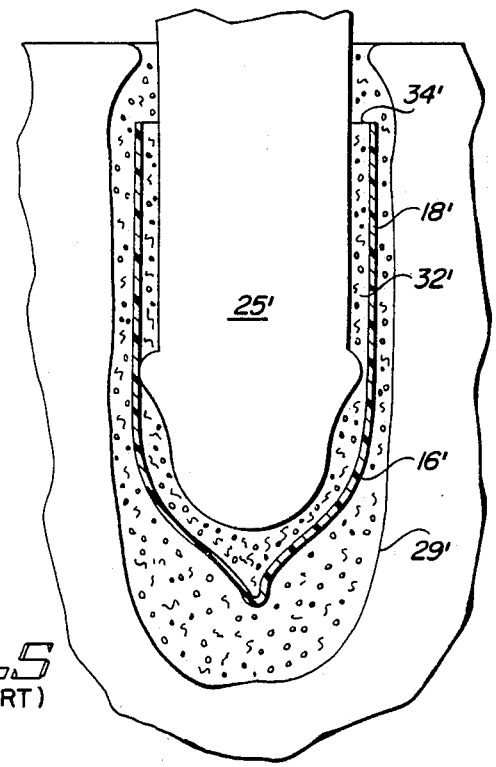
FIG. 5 is illustrative of problems which can occur with prior art condoms which do not have a pubic shield.

Referring to FIG. 5, when the penis becomes flaccid, a conventional condom 16' which does not have a shield may creep into the vagina 29' in which event the male fluids 32' may mix as at 34' with the vaginal fluids as the penis 25' becomes flaccid and the tubular portion 18' tends to creep into the vagina 29'. With the present invention during and after coitus, use of the condom of the present invention prevents exposure of the penis and vagina to infection, especially after ejaculation. The adhesive 20 may be applied as a ring, preferably, about the outer periphery of the shield and a liner also indicated by the numeral 20, since it is transparent, overlays the adhesive. Preferably, the adhesive is of the type which is readily peeled from the body without pain. Such an adhesive or skin glue, as it is sometimes called in the field, is a copolymer of an acrylic ester and acrylic acid. The adhesive is painless on removal.

The film material such as that utilized in the manufacture of the foregoing condom structure is preferably translucent, is relatively thin which provides a strong condom which is impervious to water and air, which is also sufficient to prevent the passage of germs, bacteria or virus. In the manufacture of the condom, fibrous material may be utilized for reinforcement and to strengthen the condom, especially the tubular portion.

In use with this condom, the penis is at all times out of conduct with vaginal secretions which may contain infectious organisms. The film has greater tensile strength than latex film and requires considerable force to break it. The shield portion protects the male organ by being attached to the pubic area using a suitable painless adhesive such as one which is commercially available from the Johnson & Johnson Company of New Brunswick, N.J. known as a First Aid Adhesive. The film material is less expensive than latex and an unlimited supply is available. Moreover, the film material has a longer shelf life than conventional latex condoms and does not require ideal storage conditions. The film material does not permit the passage of water or air and hence is impervious to infectious materials. Moreover, the condom tubular length provides at least as good a sexual sensuality as the latex condom and may be lubricated at the factory by commercially available K.Y. jelly inside or out, or both, before use. The jelly is preferably contained in a small aluminum packet provided with the condom. Preferably the condom is provided in three sized, small, medium and large. The shield is a circular disk preferably of about 5 inches in diameter and is part of the condom. Preferably, a liner is provided for the adhesive which can be peeled away.

As is well known, among the population there are male homosexuals and the greater strength and structure of a condom provides more protection for those who engage in such activities. It is not essential for the shield to adhere to the male body in order to be effective; however, it is preferred that adhesive be used.

While the instant invention has been shown and described in what is considered to be a preferred embodiment, it is recognized that departures may be made therefrom within the spirit and scope of this invention which is therefore not to be limited except as set forth in the claims which follow and in accordance with the doctrine of equivalents.

What is claimed is:

1. A condom of rubbery film material comprising a sleeve having an open proximal end and a closed end and being sized to receive an erect penis, said material comprising a blend of polyolefin material and thermoplastic elastomer material; said film material comprising an olefinic vulcanized blend of thermoplastic elastomer and low modulus polyolefin.

2. A condom of rubbery film material as set forth in claim 1 wherein the polyolefin comprises ultra low-density polyethylene.

3. A condom of rubbery film material comprising a blend of vulcanized polyolefin thermoplastic elastomer.

4. A condom of rubbery material comprising a sleeve having an open proximal end and a closed end and being sized to receive an erect penis, said material comprising a blend of polyolefin material and thermoplastic elastomer material, said polyolefin material comprising a linear low-density polyethylene polymer with a melt index of around 2, said index being a measure of molecular weight and of material flow in a specific heat condition.

5. A condom of rubbery material comprising a sleeve having an open proximal end and a closed end and being sized to receive an erect penis, said material comprising a blend of polyolefin material and thermoplastic elastomer material, said blend being characterized by a low modulus polyolefin comprising a co-polymer, polymerizable with other polymer molecules to form a chain.

6. A condom of rubbery film material comprising a sleeve having an open proximal end and a closed end and being sized to receive an erect penis, said material comprising a blend of polyolefin material and thermoplastic elastomer material; and said film material comprising a pair of congruent sheet peripherally heat-sealed together to form said sleeve.

7. A condom of rubbery film material comprising a sleeve having an open proximal end and a closed end and being sized to receive an erect penis, said material comprising a blend of polyolefin material and thermoplastic elastomer material; said condom including a shield extending outwardly of the open proximal end and said film material comprising a pair of congruent sheets peripherally heat-sealed together to form said sleeve.

* * * * *